United States Patent [19]

Potempa

[11] Patent Number: 5,585,349
[45] Date of Patent: Dec. 17, 1996

[54] METHOD OF TREATING VIRAL INFECTIONS

[75] Inventor: Lawrence A. Potempa, Deerfield, Ill.

[73] Assignee: Immtech International, Inc., Evanston, Ill.

[21] Appl. No.: 117,874

[22] Filed: Sep. 7, 1993

Related U.S. Application Data

[63] Continuation of Ser. No. 799,448, Nov. 27, 1991, abandoned.

[51] Int. Cl.$^6$ .................................................. A61K 39/21
[52] U.S. Cl. ................................. 514/12; 514/8; 514/21
[58] Field of Search ........................... 514/12, 8, 21

[56] References Cited

FOREIGN PATENT DOCUMENTS

WO/89/09628  10/1989  WIPO.

OTHER PUBLICATIONS

R. L. Shoeman et al, Medical Hypotheses, vol. 37, pp. 137–150 (1992).
G. Pantaleo and A. Fauci, F. of NIH Research, vol. 5, pp. 68–73 (1993).
A. S. Fauci, Science, vol. 262, pp. 1011–1018 (1993).
Medical Microbiology, 2nd Ed., ed. Samuel Baron, MD, Addison–Wesley, Pub, Inc, pp. 727–732 (1986).
Ammar et al. J. Clin Invest, '87(6), 2048–55, Biological and Biochemical Characterization . . . normal T cells.
Rudd et al PNAS, '85 pp. 5190–5194, Jul. 1988.
"The CD4 recepton . . . T lymphocytes".
Atono et al., *Gastroenterologia Japonica*, 24, 655–662 (1989).
Ballou et al., *J. Lab. Clin. Med.*, 115, 332–38 (1990).
Barna et al., *Cancer Research*, 44, 305–310 (1984).
Bray et al., *Clin. Immunol. Newsletter*, 8, 137–140 (1987).
Chase, "Doctors and Patients Hope AZT Will Help Stave Off AIDS," *Wall Street Journal*, Apr. 28, 1988, p. 14, col. 1.
*Chem. Eng. News*, Oct. 14,1991, at 17.
*Chicago Tribune*, Nov. 15, 1991, section 1, p. 5.
Chu et al., *Proc. Amer. Acad. Cancer Res.*, 29, 371a (1988).
Chu et al., *Proc. Amer. Acad. Cancer Res.*, 28, 344a (1987).
Chudwin et al., *J. Allergy Clin. Immunol.*, 77, 216a (1986).
Dagani, *Chem. Eng. News*, Nov. 23, 1987, at 41–49.
Deodhar et al., *Cancer Research*, 42, 5084–5088 (1982).
Fauci, *Science*, 239, 617–622 (1988).
Fauci et al., *Ann. Intern. Med.*, 114, 678–693 (1991).
Gotschlich, *Ann. N.Y. Acad. Sci.*, 557, 9–18 (1989).
Gupta et al., *J. Immunol.*, 137, 2173–79 (1986).
Hokama et al., *J. Bacteriology*, 83, 1017–1024 (1962).
Horowitz et al., *J. Immunol.*, 138, 2598–2603 (1987).
Hu et al., *J. Biol. Chem.*, 263, 1500–1504 (1988).
Hu et al., *Biochem.*, 25, 7834–39 (1986).
Hull et al, *Virology: Directory & Dictionary of Animal, Bacterial and Plant Viruses*, p. 191 (Stockton Press 1989).

James et al., *Dissertation Abstracts International*, 41/08–B, 2963 (1980).
Kempka et al., *J. Immunol.*, 144, 1004–1009 (1990).
Kilpatrick and Volanakis, *Immunol. Res.*, 10, 43–53 (1991).
Kilpatrick and Volanakis, *J. Immunol.*, 134, 3364–70 (1985).
Kindmark, *Clin. Exp. Immunol.*, 8, 941–48 (1971).
Lei et al., *J. Biol. Chem.*, 260, 13377–83 (1985).
Mantzouranis et al., *Ped. Res.*, 18, 260a (1984).
Mold et al., *Infection and Immunity*, 38, 392–395 (1982).
Mold et al., *Ann. N.Y. Acad. Sci.*, 389, 251–62 (1982).
Montefiori et al., *Proc. Nat'l Acad. Sci. U.S.A.*, 84, 2985–89 (1987).
Nakayama et al., *Clin. Exp. Immunol.*, 54, 319–26 (1983).
Nakayama et al., *J. Immunol.*, 132, 1336–40 1984).
Potempa et al., *Mol. Immunol.*, 20, 1165–75 (1983).
Potempa et al. *Mol. Immunol.*, 24, 531–41 (1987).
Potempa et al., *Proc. Amer. Acad. Cancer Res.*, 28, 344a (1987).
Potempa et al., *Protides Biol. Fluids*, 34, 287–290 (1986).
Potempa et al., *Inflammation*, 12, 391–405 (1988).
Potempa et al., *FASEB J.*, 2, 731a (1988).
Putto et al., *Archives of Disease in Childhood*, 61, 24–29 (1986).
Reed and Muench, *Amer. J. Hygiene*, 27, 493 (1938).
Rees et al., *Fed. Proc.*, 45, 263a (1986).
Samols and Hu, *Protides Biol. Fluids*, 34, 263–66 (1986).
Samols et al., *Biochem. J.*, 227, 759–65 (1985).
Tebo et al., *J. Immunol.*, 144, 231–38 (1990).
Thombre et al., *Cancer Immunol. Immunother.*, 16, 145–150 (1984).
Tillett and Francis, *J. Exp. Med.*, 52, 561–71 (1930).
Volanakis et al., *J. Immunol.*, 113, 9–17 (1974).
Weislow et al., *J. Natl. Cancer Inst.*, 81, 577–586 (1989).
Whitehead et al., *Biochem. J.*, 266, 283–90 (1990).
Woo et al., *J. Biol. Chem.*, 260, 13384–88 (1985).
Xia et al., *FASEB J.*, 5, A1628 (1991).
Yarchoan et al., *Anal Intern. Med.*, 115, 184–89 (1991).
Yarchoan et al., *Immunol. Today*, 11, 327–33 (1990).
Ying et al., *J. Immunol.*, 143, 221–28 (1989).
Zeller et al., *Fed. Proc.*, 46, 1033a (1987).

*Primary Examiner*—Elizabeth C. Weimar
*Assistant Examiner*—P. Lynn Touzeau
*Attorney, Agent, or Firm*—Brinks Hofer Gilson & Lione

[57] ABSTRACT

The invention provides a method of treating a viral infection in a mammal comprising administering an effective amount of modified C-reactive protein (CRP) to the mammal. In particular, modified-CRP has been found to be effective and safe for treating retroviral infections, including human immunodeficiency virus 1. The invention also provides a method of neutralizing a virus comprising contacting the virus with modified-CRP. In particular, modified-CRP can be used to neutralize viruses in blood which is to be used for transfusions by adding the modified-CRP to the blood prior to the transfusion.

1 Claim, 4 Drawing Sheets

METHOD OF TREATING VIRAL INFECTIONS

This application is a continuation of application Ser. No. 07/799,448, filed Nov. 27, 1991, now abandoned.

FIELD OF INVENTION

The invention relates to a method of treating viral infections with modified C-reactive protein. The invention also relates to a method of neutralizing viruses with modified C-reactive protein.

BACKGROUND OF THE INVENTION

Since the advent of AIDS (acquired immunodeficiency syndrome), the need for effective treatments for viral infections has become urgent. AIDS is caused by human immunodeficiency virus 1 (HIV-1). The initial pathogenic event is the binding of HIV-1 to the CD4 receptor on a subset of T cells and monocyte-macrophages. Fauci et al., *Ann. Intern. Med.*, 114, 678–693 (1991) (summary of a National Institutes of Health Conference). The virus interacts with the human immune system, and the ultimate consequence of this interaction is a profound immunosuppression resulting from the quantitative depletion and functional abnormalities of the CD4 T-cell subset. Id. Mononuclear phagocytes may play a role in the pathogenesis of HIV-1 infection by serving as reservoirs of the virus. Id. Of note is the fact that monocytes in the peripheral blood of HIV-1-infected individuals are rarely infected in vivo, whereas infected tissue macrophages may play a role in organ-specific HIV-1-related pathogenesis. Id.

One drug that has been approved by the Food and Drug Administration (FDA) for the treatment of AIDS is 3'-azido-2',3'-dideoxy-thymidine (zidovudine, azidothymidine, AZT) which inhibits HIV-1 replication by acting at the level of reverse transcriptase. However, AZT causes serious side effects, such as bone marrow suppression, and it is poorly tolerated in a high proportion of patients. Yarchoan et al., *Immunol. Today*, 11, 327–33 (1990). Also, the beneficial effects of AZT have been reported to abate in 12–18 months. Chase, "Doctors and Patients Hope AZT Will Help Stave Off AIDS," *Wall Street Journal*, Apr. 28, 1988, page 14, col. 1.

The FDA has also approved 2',3'-dideoxyinosine (DDI) for the treatment of AIDS in patients who cannot tolerate AZT or for whom AZT is no longer effective. DDI has been found efficacious and safe in the short term, but its long term effects are not yet known. *Chem. Eng. News*, Oct. 14, 1991, at 17.

Another drug for the treatment of AIDS is ampligen. Ampligen is a mispaired double-stranded RNA. It increases antiviral activity by stimulating interferon production, activating natural killer cells, and augmenting an internal cellular antiviral mechanism. Montefiori et al., *Proc. Nat'l Acad. Sci. U.S.A.*, 84, 2985–89 (1987) and Dagani, *Chem. Eng. News*, Nov. 23, 1987, at 41–49.

Other possible therapeutic approaches for the treatment of AIDS are discussed in Yarchoan et al., *Immunol. Today*, 11, 327–33 (1990); Dagani, *Chem. Eng. News*, Nov. 23, 1987, at 41–49.

C-reactive protein (CRP) was first described by Tillett and Francis [*J. Exp. Med.*, 52, 561–71 (1930)] who observed that sera from acutely ill patients precipitated with the C-polysaccharide of the cell wall of *Streptococcus pneumoniae*. Others subsequently identified the reactive serum factor as protein, hence the designation "C-reactive protein."

In addition to binding to pneumococcal C-polysaccharide, CRP binds to: 1) phosphate monoesters, including particularly phosphorylcholine; 2) other cell wall polysaccharides containing phosphorylcholine; 3) phosphatidyl choline (lecithin); 4) fibronectin; 5) chromatin; 6) histones; and 7) the 70 kDa polypeptide of the U1 small nuclear ribonucleoprotein. Kilpatrick and Volanakis, *Immunol. Res.*, 10, 43–53 (1991). Several laboratories have also reported the binding of CRP to galactose-containing polysaccharides. Id. However, one laboratory has reported that CRP binds to trace phosphate groups that are minor constituents of one particular galactan, making it is unclear whether CRP binding to other galactans is also directed to phosphate residues or to carbohydrate determinants. Id.

Atono et al., *Gastroenterologia Japonica*, 24, 655–662 (1989) teaches that the level of serum CRP is markedly increased in patients with acute hepatitis type A and type B, especially in type A, but decreases rapidly during the convalescent phase. The article also reports that the CRP level is generally low in non-A, non-B hepatitis in both the acute and convalescent phases.

Putto et al., *Archives of Disease in Childhood*, 61, 24–29 (1986) reports the results of measurements of the level of CRP in febrile children suffering from bacterial and viral infections. If the duration of the illness was more than 12 hours and the CRP level was less than 20 mg/ml, all children investigated had viral or probable viral infections. Some children with CRP levels of 20 mg/ml or less had invasive bacterial infections, but they had been sick for 12 hours or less. CRP levels between 20 mg/ml and 40 mg/ml were recorded in children with both viral and bacterial infections. A CRP value greater than, or equal to, 40 mg/ml detected 79% of bacterial infections with 90% specificity.

To Applicant's knowledge, there have been no reports of CRP binding to viruses, contributing to the phagocytosis of viruses, or otherwise being able to neutralize viruses. Moreover, Applicant is not aware of any reports of CRP being used to treat viral infections.

Much of the study of CRP has been directed to determining its role in bacterial infections. For instance, Xia et al., *FASEB J.*, 5, A1628 (1991) describes experiments designed to explore the role of CRP in endotoxin shock. A chimeric gene coding for rabbit CRP under the control of an inducible promoter (inducible in response to demand for gluconeogenesis) was introduced into mice. In contrast to most other vertebrates, mice synthesize only trace amounts of endogenous CRP, even during an acute phase response. When the chimeric gene was introduced into the mice, rabbit CRP was expressed in response to demand for gluconeogenesis. Further, it was found that 75% of mice expressing high levels of rabbit CRP following induction of gluconeogenesis survived treatment with 350–400 µg of endotoxin, as compared to 27% survival for animals in which rabbit CRP synthesis had been suppressed by inhibiting gluconeogenesis. The authors speculate that CRP may play a role in natural defense against endotoxin shock, although CRP is not known to bind endotoxin.

Mold et al., *Infection and Immunity*, 38, 392–395 (1982) reports that CRP binding can lead to complement activation and, in the presence of complement, enhancement of opsonization of C-polysaccharide-sensitized erythrocytes and type 27 *S. pneumoniae*. The article further reports that injection of CRP increased survival in mice challenged with type 3 or type 4 *S. pneumoniae*. Finally, the authors describe test results from which they conclude that CRP binds to a small group of potentially pathogenic gram-positive bacteria (*S. pneumoniae, Streptococcus viridans*, and one isolate of *Staphylococcus aureus*), but does not bind to gram-negative bacteria or to other gram-positive bacteria. They, therefore, postulate that the ability of CRP to enhance opsonization and contribute to host defense may be specific for infection with *S. pneumoniae*.

Similarly, Mold et al., *Ann. N.Y. Acad. Sci.*, 389, 251–62 (1982) reports that CRP can act as an opsonin in the presence of complement. However, the article teaches that CRP does not bind to gram-negative bacteria and binds to only some gram-positive organisms. For those gram-positive bacteria to which CRP binds, the effectivenss of CRP as an opsonin varied depending on the species. Finally, the article reports that CRP protected mice from type 3 and type 4 *S. pneumoniae* infection.

Nakayama et al., *Clin. Exp. Immunol.*, 54, 319–26 (1983) also teaches that CRP protects against lethal infection with type 3 or type 4 *S. pneumoniae*. The article further teaches that CRP did not protect against a similar dose of Salmonella typhimurium LT2.

Horowitz et al., *J. Immunol.*, 138, 2598–2603 (1987) describes the effects of CRP in mice with a X-linked immunodeficiency ("xid mice") which prevents the mice from making antibodies to polysaccharide antigens. In these mice, CRP provided protection against infection with type 3 *S. pneumonia* and acted by clearing the bacteria from the blood. However, CRP was not completely protective at higher doses of *S. pneumoniae*. Since CRP provides complete protection against these doses in normal mice, the authors speculated that CRP's function is to slow the development of pneumococcal bacteremia until protective antibodies to capsular polysaccharide can be produced. C3 depletion decreased or abrogated the protective effects of CRP in xid mice, but not in normal mice.

Nakayama et al., *J. Immunol.*, 132, 1336–40 1984) reports the results of injecting mice with CRP and then immunizing them with type 3 *S. pneumococci*. The result was a diminished antibody response to the phosphorylcholine determinants on the bacteria which varied with the dose of CRP. However, antibodies were formed to other antigenic determinants on the *S. pneumococci*.

Hokama et al., *J. Bacteriology*, 83, 1017–1024 (1962) reports that carbonyl iron spherules, *Diplococcus pneumoniae* types IIs and XXVIIs and *Serratia marcescens* were phagocytosed more rapidly and in greater numbers by leukocytes of normal human blood after incubation with CRP. Similarly, Kindmark, *Clin. Exp. Immunol.*, 8, 941–48 (1971) reports that CRP stimulated phagocytosis of *Diplococcus pneumoniae, Staphylococcus aureus, Escherichia coli* and *Klebsiella aerogenes*.

Gupta et al., *J. Immunol.*, 137, 2173–79 (1986) teaches that CRP has been detected in immune complexes isolated from the sera of patients with acute rheumatic fever. Rheumatic fever is an acute inflammatory disease that may follow group A streptococcal pharyngitis. The other components of the immune complexes included streptolysin O and antibodies to streptolysin O.

However, Ballou et al., *J. Lab. Clin. Med.*, 115, 332–38 (1990) teaches that highly purified CRP does not bind to immunoglobulin (monomeric or aggregated) or immune complexes. The article suggests that the reported presence of CRP in immune complexes may result from, or be facilitated by, an association of CRP with components of the immune complexes other than immunoglobulin, such as antigens or complement components.

Kilpatrick and Volanakis, *J. Immunol.*, 134, 3364–70 (1985) reports that there is a CRP receptor on stimulated polymorphonuclear leukocytes (PMN). The authors also disclose that the ingestion of erythrocytes coated with pneumococcal C-polysaccharide and CRP by activated PMN is greater than ingestion of erythrocytes coated only with pneumococcal C-polysaccharide. Finally, the authors propose that CRP's function relates to its ability to specifically recognize foreign pathogens and damaged or necrotic host cells and to initiate their elimination by 1) interacting with the complement system or 2) interacting with inducible phagocytic receptors on neutrophils.

James et al., *Dissertation Abstracts International*, 41/08-B, 2963 (1980) teaches that CRP binds to a subset of mononuclear leukocytes, including 40% of the phagocytic monocytes and 3% of lymphocytes. Binding was influenced by several factors, including the form of the CRP molecule (i,e., modification of the CRP was required, either by complexing to a ligand or by heating to 63° C.).

Tebo et al., *J. Immunol.*, 144, 231–38 (1990) teaches the presence of a receptor for CRP on monocytes. The article further discloses that a membrane receptor for CRP has been reported on neutrophils.

Kempka et al., *J. Immunol.*, 144, 1004–1009 (1990) discloses results which the authors interpret to mean that CRP is a galactose-specific binding protein which, when associated to the surface of liver macrophages, functions as a receptor mediating galactose-specific endocytosis of particulate ligands.

CRP is a pentamer which consists of five identical subunits. The pentameric form of CRP is sometimes referred to as "native CRP." In about 1983, another form of CRP was discovered which is referred to as "modified-CRP" or "mCRP". mCRP has significantly different charge, size, solubility and antigenicity characteristics as compared to native CRP. Potempa et al., *Mol. Immunol.*, 20, 1165–75 (1983). mCRP also differs from native CRP in binding characteristics; for instance, mCRP does not bind phosphorylcholine. Id.; Chudwin et al., *J. Allergy Clin. Immunol.*, 77, 216a (1986). Finally, mCRP differs from native CRP in its biological activity. See Potempa et al., *Protides Biol. Fluids*, 34, 287–290 (1986); Potempa et al., *Inflammation*, 12, 391–405 (1988).

The distinctive antigenicity of mCRP has been referred to as "neo-CRP." Neo-CRP antigenicity is expressed on:

1) CRP treated with acid, urea or heat under certain conditions (described below);

2) the primary translation product of DNA coding for CRP (preCRP); and

3) CRP immobilized on plastic surfaces. Potempa et al., *Mol. Immunol.*, 20, 1165–75 (1983); Mantzouranis et al., *Ped. Res.*, 18, 260a (1984); Samols et al., *Biochem. J.*, 227, 759–65 (1985); Chudwin et al., *J. Allergy Clin. Immunol.*, 77, 216a (1986); Potempa et al., *Inflammation*, 12, 391–405 (1988).

A molecule reactive with polyclonal antibody specific for neo-CRP has been identified on the surface of 10–25% of peripheral blood lymphocytes (predominantly NK and B cells), 80% of monocytes and 60% of neutrophils, and at sites of tissue injury. Potempa et al., *FASEB J.*, 2, 731a (1988); Bray et al., *Clin. Immunol. Newsletter*, 8, 137–140 (1987); Rees et al., *Fed. Proc.*, 45, 263a (1986). In addition, it has been reported that mCRP can influence the development of monocyte cytotoxicity, improve the accessory cell function of monocytes, potentiate aggregated-IgG-induced phagocytic cell oxidative metabolism, and increase the production of interleukin-1, prostaglandin E and lipoxygenase products by monocytes. Potempa et al., *Protides Biol. Fluids*, 34, 287–290 (1987); Potempa et al., *Inflammation*, 12, 391–405 (1988); Chu et al., *Proc. Amer. Acad. Cancer Res.*, 28, 344a (1987); Potempa et al., *Proc. Amer. Acad. Cancer Res.*, 28, 344a (1987); Zeller et al., *Fed. Proc.*, 46, 1033a (1987); Chu et al., *Proc. Amer. Acad. Cancer Res.*, 29, 371a (1988).

Chudwin et al., *J. Allergy Clin. Immunol.*, 77, 216a (1986) teaches that mCRP can have a protective effect in mice challenged with gram-positive type 7F *S. pneumoniae*. Mice were injected intravenously with saline, native CRP, or mCRP. Thirty minutes later the mice received a lethal dose of *S. pneumoniae*. Survival at 10 days was as follows: 2/18 mice pretreated with saline; 7/12 mice pretreated with 200 µg of native CRP; 12/18 mice pretreated with 10 µg mCRP; and 5/6 mice pretreated with 100 µg of mCRP. The authors speculate that CRP may be protective against bacterial infections by mechanisms other than phosphorylcholine binding and that CRP may have a wider role in bacterial host defenses than previously suspected through mCRP (which does not bind phosphorylcholine).

To Applicant's knowledge, there have been no reports that mCRP is protective against any other kind of bacterial infection. Moreover, to Applicant's knowledge, there have been no reports of mCRP binding to viruses, contributing to the phagocytosis of viruses, otherwise being able to neutralize viruses, or being used to treat viral infections.

For a brief review of CRP and mCRP, see Gotschlich, *Ann. N.Y. Acad. Sci.*, 557, 9–18 (1989). Kilpatrick and Volanakis, *Immunol. Res.*, 10, 43–53 (1991) provides a recent review of CRP.

Finally, Applicant wishes to draw attention to certain co-pending applications on which he is named as a co-inventor. U.S. application Ser. No. 07/582,884, filed Oct. 3, 1990, relates to the use of mCRP to bind immune complexes. This application was filed as a national application of PCT application US89/01247 (published as WO 89/09628 on Oct. 19, 1989) and is a continuation-in-part of U.S. application Ser. No. 07/176,923, filed Apr. 4, 1988, now abandoned. Applicant is also named as a co-inventor on U.S. application Ser. No. 07/374,166, filed Jun. 29, 1989, a continuation-in-part of application Ser. No., 07/372,442 filed Jun. 27, 1989, now abandoned. This application describes and claims monoclonal antibodies selectively reactive with epitopes found on native CRP, mCRP or both. Finally, being filed on even date herewith is an application entitled "Method Of Treating Non-Streptococcal Bacterial Infections" which relates to the use of mCRP to treat such infections.

SUMMARY OF THE INVENTION

The invention provides a method of treating a viral infection in a mammal comprising administering to the mammal an effective amount of modified-CRP in a pharmaceutically-acceptable carrier. In particular, modified-CRP has been found effective in treating Retroviridae infections, including human immunodeficiency virus 1 (HIV-1) infections.

The invention also provides a method of neutralizing a virus comprising contacting the virus with modified-CRP. For instance, modified-CRP can be used to neutralize viruses in a blood sample which is to be used for a transfusion by adding the modified-CRP to the blood sample prior to the transfusion. In particular, modified-CRP has been found effective in neutralizing Retroviridae, including HIV-1.

DETAILED DESCRIPTION OF THE PRESENTLY PREFERRED EMBODIMENTS

The modified-CRP useful in the practice of the invention may be from any species. There is substantial homology between the amino acid sequences of CRP's from different species. For instance, there is from about 50 to about 80% sequence homology between CRP's from various mammalian species. Hu et al., *Biochem.*, 25, 7834–39 (1986); Whitehead et al., *Biochem. J.*, 266, 283–90 (1990); Kilpatrick and Volanakis, *Immunol. Res.*, 10, 43–53 (1991). It is, therefore, expected that mCRP from any species will be effective in treating viral infections or neutralizing viruses. Thus, a mammal suffering from a viral infection may be treated with mCRP from a different species (e.g., mice can be treated with human mCRP). Alternatively, and preferably, the mammal is treated with homologous mCRP (e.g., humans are treated with human mCRP) to avoid immune reactions to the mCRP.

mCRP is preferably made using CRP as a starting material. Methods of isolating CRP from natural sources are well known. Many such techniques are described in the references discussed in the Background section. CRP is preferably isolated from pleural or ascites fluid by calcium-dependent affinity chromatography using phosphorylcholine-substituted BioGel A 0.5 m (an agarose-based resin obtained from BioRad Laboratories) as described by Volanakis, et al. [*J. Immunol.*, 113, 9–17 (1978)] and modified by Potempa, et al. [*Mol. Immunol.*, 24, 531–41 (1987)]. Using this procedure, CRP can be obtained which is at least 99% pure.

Genomic and cDNA clones coding for human, mouse, and rabbit CRP have been isolated. Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Hu et al., *J. Biol. Chem.*, 263, 1500–1504 (1988); Whitehead et al., *Biochem. J.*, 266, 283–90 (1990). Given the substantial homology between CRP's from different species, probes can readily be prepared so that genomic and cDNA clones can be isolated which code for CRP's from other species. Methods of preparing such probes and isolating genomic and cDNA clones are well known. See, e.g., Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Hu et al., *J. Biol. Chem.*, 263, 1500–1504 (1988); Whitehead et al., *Biochem. J.*, 266, 283–90 (1990). Using one of the known clones or a newly-isolated clone, CRP can be prepared using conventional and well known recombinant DNA techniques and cell culture and fermentation conditions. See, e.g., Hu et al., *J. Biol. Chem.*, 263, 1500–1504 (1988). However, to obtain pentameric native CRP, eukaryotic host cells, preferably mammalian host cells should be used. See Samols and Hu, *Protides Biol. Fluids*, 34, 263–66 (1986); Hu et al., *J. Biol. Chem.*, 263, 1500–1504 (1988).

Methods of making mCRP from CRP are well known. Many such methods are described in the references discussed in the Background section.

For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11–12. Finally, mCRP can be produced by heating CRP above 50° C. for a time sufficient to cause denaturation (preferably at 63° C. for 2 minutes) in the absence of calcium or in the presence of a chelator such as those listed above.

mCRP can also be prepared using recombinant DNA techniques. As noted in the Background section, the primary translation product of the CRP gene (preCRP) has been found to express neo-CRP antigenicity. Accordingly, mCRP can be prepared by selecting conditions so that that the CRP subunits are not assembled into pentameric native. CRP in the host cell. This can be accomplished by expressing the desired genomic or cDNA clone in a prokaryotic host. See Samols and Hu, *Prot. Biol. Fluids*, 34, 263–66 (1986). The mCRP produced in this manner appears to consist of aggregates of CRP subunits and/or preCRP and perhaps other CRP peptides. See id. This form of mCRP is insoluble, and further purification is problematical. However, it should be possible to inject this insoluble material directly into mammals as a suspension without further processing since suspensions of isolated mCRP prepared from CRP have been found safe and effective when injected into mammals (see Example 2).

Finally, mCRP can be prepared by adsorbing CRP to hydrophobic solid surfaces. Suitable solid surfaces and conditions are described in co-pending application Ser. No. 07/582,884 and PCT application WO 89/09628, the disclosures of which are incorporated herein by reference. mCRP adsorbed to solid surfaces may be useful in removing viruses from fluids, such as blood, as discussed below.

mCRP may be distinguished from native CRP by several criteria. As noted in the Background section, modified CRP expresses neo-CRP antigenicity, whereas native CRP does not. Neo-CRP antigenicity can be detected using polyclonal antisera specific for neo-CRP as described in the Background section. Preferably, however, mCRP is distinguished from native CRP using monoclonal antibodies like those described in Applicant's co-pending application Ser. No. 07/374,166, the disclosure of which is incorporated herein by reference. These monoclonal antibodies are also described in Ying et al., *J. Immunol.*, 143, 221–28 (1989). mCRP also binds immune complexes and aggregated immunoglobulin, whereas native CRP does not as described in Applicant's co-pending application Ser. No. 07/582,884 and published PCT application WO 89/09628. There are also several other ways to distinguish mCRP from native CRP including charge, solubility, binding characteristics and biological activity as discussed in the Background section. However, to show that a preparation contains mCRP, it is usually sufficient to establish that the preparation 1) reacts positively with an antibody specific for an epitope found only on mCRP and 2) binds aggregated immunoglobulin (e.g., aggregated IgG).

Although not wishing to be bound by any particular theory, it is believed that mCRP is formed by the dissociation of the five CRP subunits, each of which then undergoes a spontaneous conformational change to form mCRP. See Bray et al., *Clin. Immunol. Newsletter*, 8, 137–140 (1987). Accordingly, it is possible that fragments of the CRP subunits may have the same activities described herein for mCRP, and the use of such fragments would come within the scope of the present invention.

It is also believed that proteins substantially homologous to CRP will have the activities described herein for mCRP, and such proteins are also considered to come within the scope of the invention. For instance, CRP subunits having a few amino acids added, deleted or substituted by, e.g., site-directed mutagenesis of the CRP gene, would likely be effective in the treatment of viral infections and could be substituted for mCRP. In particular, mCRP is defined herein to include the primary translation product of the CRP gene.

It is contemplated that mCRP can be used to treat any type of viral infection. However, it is particularly noteworthy that mCRP has been found effective and safe in treating Retroviridae infections. mCRP has been found to provide significant protection against HIV-1 infection in the standardized in vitro test performed by the National Cancer Institute (NCI), while exhibiting no toxicity at any dose tested. mCRP has also been found to significantly reduce simian immunodeficiency virus (SIV) titers and increase the number of CD4 cells in monkeys in a manner comparable or superior to AZT, but without any side effects.

The Retroviridae are a family of spherical enveloped RNA viruses comprising three sub-families: Oncovirinae, Spurmavirinae and Lentivirinae. Hull et al, *Virology: Directory & Dictionary of Animal, Bacterial and Plant Viruses*, page 191 (Stockton Press 1989). The particles are 80–100 nm in diameter with glycoprotein surface projections of 8 nm. Id. Replication starts with reverse transcription of virus RNA into DNA which becomes integrated into the chromosomal DNA of the host. Id.

Endogenous oncoviruses occur widely among vertebrates and are associated with many diseases. Id. Transmission is both vertical and horizontal. Id.

The lentiviruses include HIV-1 and SIV. Fauci, *Science*, 239, 617–622 (1988). Of particular note are HIV-i's morphological, biological and molecular similarities to the visna virus of sheep, equine infectious anemia virus, and feline immunodeficiency virus. Id. HIV-1 is also related to other primate retroviruses such as STLV-III (believed to be the same as SIV). Id. HIV-2 shares serological reactivity and polynucleotide sequence homology with STLV-III and has been isolated from West African patients with a clinical syndrome indistinguishable from HIV-1-induced AIDS and AIDS-related condition (ARC) . Id.

To treat viral infections in a mammal, an effective amount of mCRP is administered to the mammal. The mCRP is preferably administered to the mammal before the infection becomes too serious. Most preferably, the mCRP is administered at the first indication of a viral infection or prophylactically to those at risk of developing viral infections. For instance, mCRP may be administered prophylatically to hemophiliacs or surgical patients who may receive blood contaminated with a virus such as HIV-1. Indeed, it is contemplated that mCRP can be added to blood bags, preferably at the time that blood is drawn, to neutralize any viruses, especially HIV-1, which may be present in the blood and to, thereby, prevent transmission of the virus to those who receive transfusions. Of course, mCRP can be administered to a mammal already suffering from a viral infection.

mCRP will generally be administered to the mammal by injection (e.g., intravenous, intraperitoneal, subcutaneous, intramuscular) or encapsulated in liposomes. Preferably intravenous injection is used. mCRP may also be applied topically to, e.g., a wound or other site of infection. Finally, it should be possible to administer mCRP by means of a spray to treat respiratory infections. It should be noted that it is unlikely that mCRP can be administered orally since it is a protein.

It is understood by those skilled in the art that the dose of mCRP that must be administered will vary depending on the mammal which will receive the mCRP, the type of infection, the seriousness of the infection, the route of administration, and the identity of any other drugs being administered to the mammal. It is also understood that it may be necessary to give more than one dose of mCRP.

Effective dosages and schedules for administration of mCRP may be determined empirically, and making such determinations is within the skill of the art. Applicant has found that a dose of from about 5 µg to about 150 mg of mCRP per kg, preferably from about 250 µg to about 15 mg per kg, is effective for treating viral infections. Generally, several such doses of mCRP must be given to the mammal, and the interval between doses is preferably from about 1 day to about 7 days. Administration of mCRP should be continued until health has been restored to the mammal.

Pharmaceutically-acceptable carriers are well known. For instance, suitable carriers for the administration of mCRP include fluids such as water, saline and buffers. Preferably, phosphate buffered saline, pH 7.4, is used as the carrier. mCRP may also be administered encapsulated in liposomes [see Deodhar et al., *Cancer Research*, 42, 5084–5088 (1982); Thombre et al., *Cancer Immunol. Immunother.*, 16, 145–150 (1984); Barna et al., *Cancer Research*, 44, 305–310 (1984)]. For topical application, mCRP may be incorporated into lotions, gels, cremes, etc., as is well known in the art.

It is not known yet how mCRP exerts its antiviral effects. It may act on, or interact with, the immune system of the mammal to make it more effective in coping with the viral infection. In addition, it is believed highly likely that mCRP binds to viruses.

If so, mCRP could be used in an assay for detecting or quantitating viruses. For instance, mCRP could be used in assays such as those described in co-pending application Ser. No. 07/582,884. For example, mCRP could be bound to a solid surface and used to bind virus in a body fluid. After washing away unbound material, the virus could be detected or quantitated using a labeled antibody to the virus. Alternatively, the antiviral antibody could be bound to the solid surface, and the mCRP could be labeled.

mCRP can also be used to neutralize viruses present in fluids such as blood. As noted above, it is contemplated that mCRP can be added to blood bags, preferably at the time that blood is drawn, to neutralize any viruses, especially HIV-1, which may be present in the blood and to, thereby, prevent transmission of the virus to those who receive transfusions. Preliminary data from experiments in which mCRP was added to blood to which HIV-1 was subsequently added indicate that mCRP reduced infectivity. Alternatively, mCRP could be bound to a solid surface, such as in a plasmapheresis device, as described in co-pending application Ser. No. 07/582,884, and blood or other fluid can be passed through the device to remove the virus.

Finally, it is contemplated that mCRP can be used as an adjuvant in vaccines designed to elicit protection against viruses. The ability of mCRP to neutralize viral infectivity should make such vaccines safer.

EXAMPLES

EXAMPLE 1: Activity of Modified-CRP Against HIV-1 in Vitro

A. Preparation Of modified-CRP

Human CRP was isolated from pleural or ascites fluid by calcium-dependent affinity chromatography using phosphorylcholine-substituted BioGel A 0.5m (an agarose-based resin obtained from BioRad Laboratories) as described by Volanakis, et al. [*J. Immunol.*, 113, 9–17 (1978)] and modified by Potempa, et al. [*Mol. Immunol.*, 24, 531–41 (1987)]. Briefly, the pleural or ascites fluid was passed over the phosphorylcholine-substituted column, and the CRP was allowed to bind. Then, the column was exhaustively washed with 75 mM Tris-HCl-buffered saline (pH 7.2) containing 2 mM $CaCl_2$ until the absorbance at 280 nanometers was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations.

CRP-containing fractions were pooled, diluted three-fold with deionized water, adsorbed to DE52 ion exchange resin (from Whatman), and then eluted with a linear salt gradient of from 0.05 M to 0.5 M NaCl. CRP-containing fractions were pooled and re-calcified to 2–5mM $CaCl_2$ (by adding a suitable amount of a 1M solution) and applied to unsubstituted Biogel A 0.5m column to remove residual serum amyloid P component (SAP).

Next, the CRP was concentrated to 1 mg/ml using ultra-filtration (Amicon; PM30 membrane) under 10–20 psi nitrogen. A CRP extinction coefficient (mg/ml) of 1.98 was used to determine concentration. Next, the concentrated CRP was exhaustively dialyzed in 10 mM Tris-HCl-buffered saline (pH 7.2) containing 2 mM $CaCl_2$, sterile-filtered and stored at 4° C. These preparations produced a single Mr 23,000 band on SDS-PAGE electrophoresis and were more than 99% free of SAP, IgG and all other proteins tested for antigenically.

To make mCRP, the CRP (prepared as described above) at 1 mg/ml was incubated in 8 M ultra-pure urea (Schwartz-Mann, Spring Valley, N.Y.) in the presence of 10 mM EDTA for one hour at 37° C. The urea was removed by dialysis into 10 mM sodium phosphate buffer (pH 7.4) or Tris-HCl buffer (pH 7.2) containing 0.015 M sodium chloride; more than 90% of the starting protein was accounted for in the solution phase after dialysis.

The mCRP was sterile filtered through a 0.20 micron filter (Gelman). The concentration was then adjusted to 0.5 mg/ml with 10 mM sodium phosphate buffer, pH 7.4, containing 0.015 M sodium chloride to produce a solution of mCRP. This solution is referred to herein as "soluble mCRP".

Some of the sterile-filtered soluble mCRP was adjusted to physiologic ionic strength by adding sodium chloride to give a final concentration of 0.15 M NaCl and then incubated in an ice bath for 15 minutes. The majority of the mCRP self-aggregated to form an opalescent solution which was centrifuged at about 5000 x g for 10 minutes to sediment the protein. The sedimented protein was resuspended in an appropriate volume of sterile buffer (preferably 10mM sodium phosphate buffer, pH 7.4, containing 0.15M NaCi) to give a final concentration of mCRP of 2–4 mg/ml. This suspension is referred to herein as "mCRP suspension".

B. In Vitro Assay

Soluble mCRP and mCRP suspension, prepared as described in Part A, were submitted to the National Cancer Institute (NCI) for testing in their standardized in vitro assay for activity against HIV-1. The assay used by the NCI is that described in Weislow, et al., *J. Natl. Cancer Inst.*, 81, 577–586 (1989). This procedure is designed to detect agents acting at any stage of the virus reproductive cycle. Agents that interact with virions, cells, or virus gene-products so as to interfere with viral activities will protect cells from cytolysis.

Briefly, the assay was performed as follows. Serial dilutions of mCRP in cell culture medium were prepared. T4 lymphocytes (CEM cell line) were added and, after a brief interval, HIV-1 was added. The cultures were incubated at 37° C. in a 5% carbon dioxide atmosphere for 6 days. Then a tetrazolium reagent (2,3-bis[2-methoxy-4-nitro-5-sulfophenyl]-5-[(phenylamino)carbonyl]-2H-tetrazolium hydroxide) was added to all wells, and the cultures were incubated to allow formazan color development by viable cells. Individual wells were analyzed spectrophotometrically to quantitate formazan production, and were viewed microscopically to detect viable cells and confirm protective activity. Virus-infected cells treated with mCRP were compared with uninfected cells treated with mCRP (toxicity control) and with other appropriate controls (untreated infected, untreated noninfected cells, mCRP wells without cells, etc.) on the same plate. All tests were compared with a positive control (AZT-treated) done at the same time under identical conditions.

The results of the assay are shown in FIGS. 1A–E. In those figures, the solid line connecting the diamond symbols depicts the percentage of surviving HIV-1 infected cells treated with mCRP or AZT relative to uninfected, untreated controls. The dashed line connecting the triangular symbols depicts the percentage of surviving uninfected cells treated with mCRP or AZT relative to the same uninfected, untreated controls (toxicity control). The viral cytopathic effect is indicated by the dotted reference line. This line shows the extent of destruction of cells by the virus in the absence of treatment and is used as a quality control parameter. Survival values of this parameter less than 50% are considered acceptable. The percent of protection is presented on the right side of the graph.

Figure 1A:
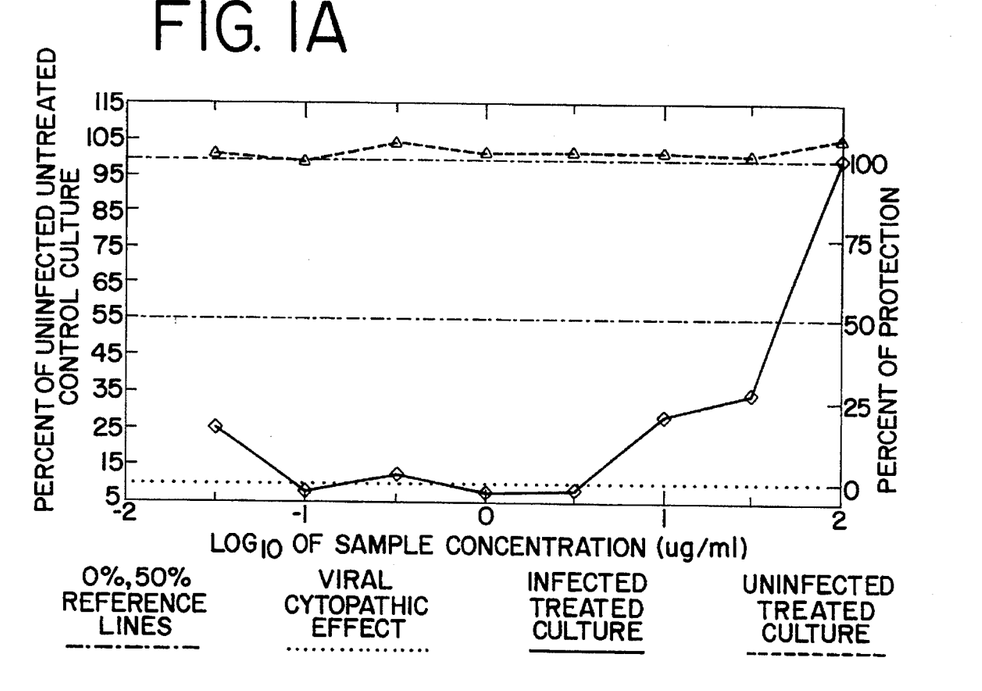
FIGS. 1A and 1B: Graphical representation of the results of two in vitro formazan assays for activity of an mCRP suspension against HIV-1.
Figure 1B:
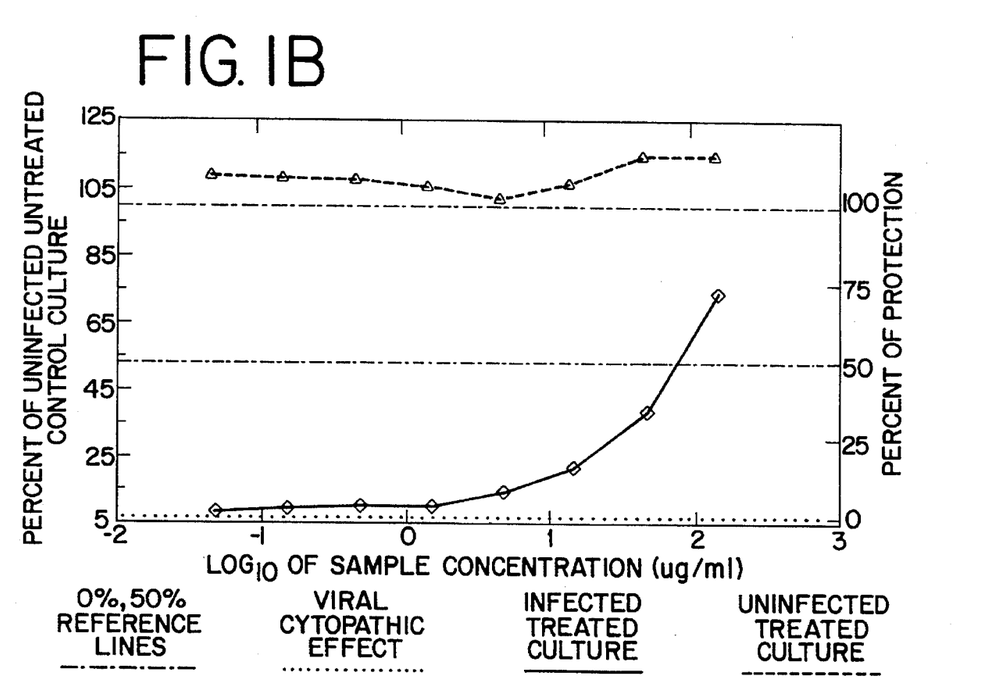
Figure 1C:
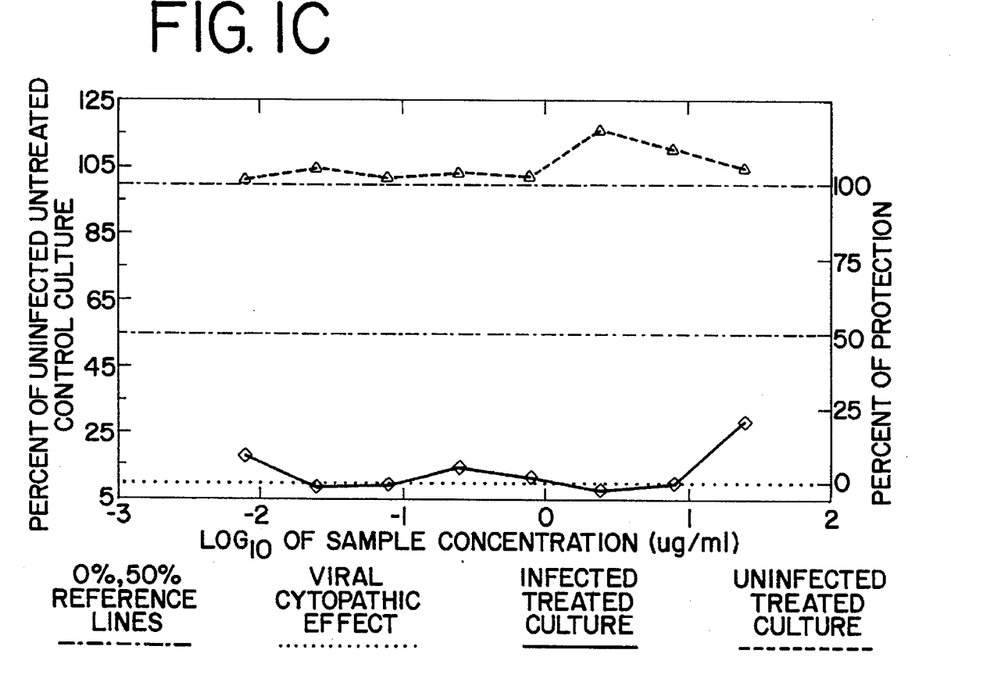
FIGS. 1C and 1D: Graphical representation of the results of two in vitro formazan assays for activity of soluble mCRP against HIV-1.
Figure 1D:
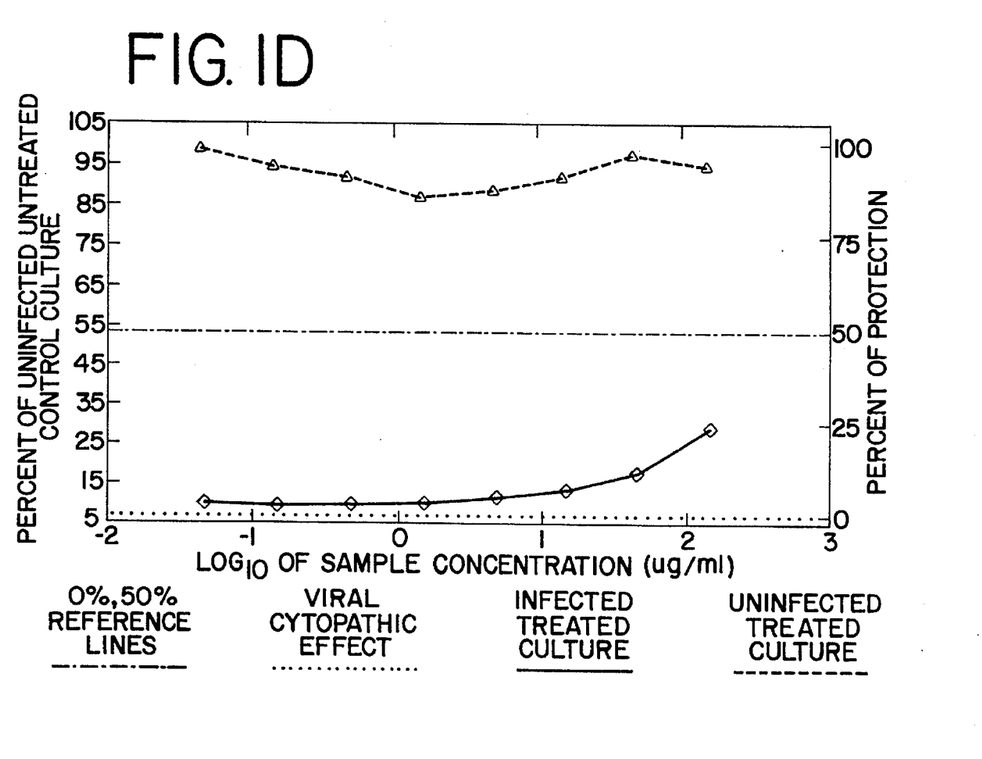
Figure 1E:
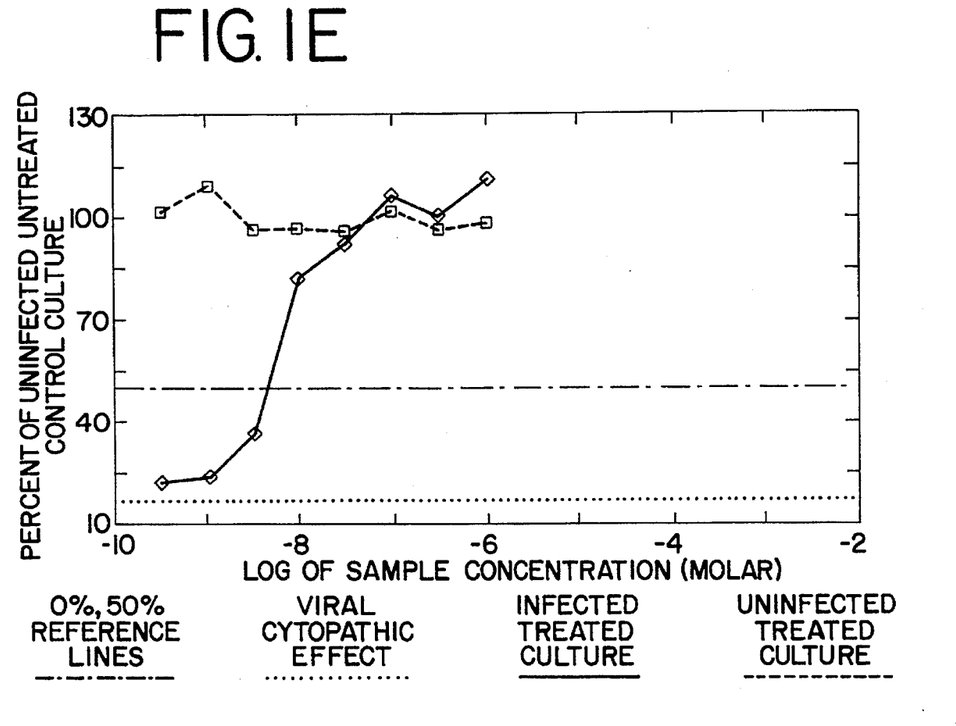
FIG. 1E: Graphical representation of the results of an in vitro formazan assay for activity of AZT against HIV-1.

As is shown in FIGS. 1A–1D, mCRP had excellent anti-HIV-1 activity. mCRP gave as much as 73–100% protection at 100–150 μg/ml (see FIGS. 1A and 1B). Also, mCRP exhibited little or no toxicity for the T4 cells at any dose tested.

An approximate value for 50% effective concentration ($EC_{50}$) was calculated by NCI as 45 μg/ml. The 50% inhibitory concentration ($IC_{50}$) could not be calculated since little or no inhibition by mCRP alone was detected. These results compare very favorably with those obtained with the AZT control (see FIG. 1E).

EXAMPLE 2: Use of modified-CRP to Treat an SIV Infection in Monkeys mCRP was tested in vivo for activity against simian immunodeficiency virus (SIV). Two male rhesus (Macaca mulatta) monkeys (designated 2B and 50B) having an established SIV infection were used. They both had been given approximately 1000 $TCID_{50}$ SIVmac251 virus about 10 months before treatment with mCRP was begun. They had been treated unsuccessfully with another experimental drug (identity unknown), but they had received no treatments of any kind for at least one month before being given mCRP to "wash out" the other drug.

Each monkey was given an intravenous injection of 16 mg of mCRP suspension (prepared as described in Example 1, part A) each day for 5 consecutive days (for a total of 80 mg/5.5–5.9 kg monkey). The first day of treatment was designated day 1.

Clinical observations were performed once daily for 19 days. Complete physical examinations were performed on day 1 prior to treatment and on day 19. Limited physical examinations (temperature, pulse and respiration) were performed on days 3, 5 and 12.

Blood samples were drawn just prior to injection of mCRP on days 1, 3 and 5. Blood samples were also drawn on days 12 and 19. The blood samples were analyzed by Fluorescence Activated Cell Sorting (FACS) to determine the percentages of various lymphocyte subsets. Viral titers and the amount of SIV p27 core protein were also determined. Routine hematological and blood chemistry tests were performed on the blood samples drawn on days 1, 5 and 19 to determine if the animals were suffering any adverse effects as a result of the treatment with mCRP.

FACS was performed on whole blood according to the manufacturer's (Becton Dickinson's) instructions. Briefly, 10–20 μl of antibody were added to 100 μl of blood containing EDTA, and the mixture was incubated in the dark for 10 minutes. Then 2 ml of FACS lysing solution (Becton Dickinson) were added, and incubation was continued for 10 minutes at room temperature. Cells were washed once in Minimum Essential Medium containing 5% fetal calf serum and were then fixed in 0.5% paraformaldehyde. Samples were analyzed on a Becton Dickinson FACScan cytometer.

Levels of T-lymphocytes bearing the CD4 marker are lowered as a result of SIV infection, just as in an HIV-1 infection. Yarchoan et al., *Anal Intern. Med.*, 115, 184–89 (1991). Normal values for monkeys are reported to be about 450 out of 1500 total lymphocytes (30–32%). Very recently, the Center for Disease Control proposed that the definition of AIDS be changed to be anyone with a CD4 lymphocyte count of 200 (14%) or less. *Chicago Tribune*, Nov. 15, 1991, section 1, page 5. Anyone with values as low as this is considered severely immunocompromised.

The percent CD4 lymphocytes in monkey 50B's blood on days 1, 3, 5, 12 and 19 obtained using anti-CD4 monoclonal antibody OKT4*a* (Ortho) are presented in Table 1 below. This monkey started on day 1 with 22.3% CD4 lymphocytes; thus, its CD4 levels were depressed but were not at an "AIDS level." During treatment (days 3 and 5) the percent CD4 levels increased 17.9% on day 3 and 10.3% on day 5 compared to starting levels on day 1. During the "wash out" period after treatment with mCRP was stopped, the percent CD4 levels fell below the day 1 value.

The results for monkey 2B are also presented in Table 1. Monkey 2B began the study on day 1 with 14.7% CD4 lymphocytes and was, therefore, near the "AIDS level". The percent CD4 level was up 12.2% on day 3 and 17.7% on day 5 after treatment with mCRP compared to the starting level. The percent CD4 levels fell below starting levels during the 2-week "washout" period.

A 5% rise in the percent CD4 levels over months of treatment with AZT is considered excellent (Dr. R. Murphy, personal communication). Hence, the observed rise of about 10–18% in CD4 levels in both monkeys 2B and 50B within hours of treatment with mCRP is considered extremely good.

TABLE 1

Determination Of CD4 Lymphocytes With OKT4a

| Monkey | Day | CD4 Lymphocytes | | % Change | |
|---|---|---|---|---|---|
| | | Absolute No. CD4 Cells Per µl* | % CD4 Cells | Absolute No. CD4 Cells Per µl | % CD4 Cells |
| 2B | 1 | 479 | 14.7 | — | — |
| | 3 | 835 | 16.5 | 74.3 | 12.2 |
| | 5 | 678 | 17.3 | 41.5 | 17.7 |
| | 12 | 529 | 12.4 | 10.4 | −15.6 |
| | 19 | 446 | 12.5 | −6.9 | −15.0 |
| 50B | 1 | 1092 | 22.3 | — | — |
| | 3 | 1330 | 26.3 | 21.8 | 17.9 |
| | 5 | 952 | 24.6 | −12.8 | 10.3 |
| | 12 | 1091 | 20.7 | 0.0 | −7.2 |
| | 19 | 546 | 21.4 | −50.0 | −4.0 |

*Absolute numbers of CD4 lymphocytes determined by multiplying total number of lymphocytes and monocytes by percentage of CD4 cells.

Leu3a, a different monoclonal antibody specific for CD4, was also used to monitor CD4 lymphocytes. The results are presented in Table 2 below. For monkey 50B, the pattern of changes in percent CD4 lymphocytes was similar to that obtained with OKT4a. Monkey 2B exhibited a different pattern. The percent CD4 lymphocytes remained relatively unchanged during the treatment period, but dropped substantially after treatment was stopped. However, the absolute numbers of CD4 lymphocytes per µl measured for monkey 2B increased during treatment (days 3 and 5) with mCRP.

TABLE 2

Determination Of CD4 Lymphocytes With Leu3a

| Monkey | Day | CD4 Lymphocytes | | % Change | |
|---|---|---|---|---|---|
| | | Absolute No. CD4 Cells Per µl* | CD4 Cells | Absolute No. CD4 Cells Per µl | % CD4 Cells |
| 2B | 1 | 572 | 17.6 | — | — |
| | 3 | 827 | 16.4 | 44.6 | −6.8 |
| | 5 | 691 | 17.6 | 20.8 | 0.0 |
| | 12 | 562 | 13.1 | −1.7 | −25.6 |
| | 19 | 491 | 13.8 | −14.2 | −21.6 |
| 50B | 1 | 990 | 20.2 | — | — |
| | 3 | 1382 | 27.4 | 39.6 | 35.6 |
| | 5 | 937 | 24.2 | −5.4 | 19.8 |
| | 12 | 1044 | 19.8 | 5.5 | −2.0 |
| | 19 | 525 | 20.6 | −47.0 | 2.0 |

*Absolute numbers of CD4 lymphocytes determined by multiplying total number of lymphocytes and monocytes by percentage of CD4 cells.

The levels of CD8 lymphocytes were also measured using anti-CD8 antibody Leu2a (Becton Dickinson). The results are presented in Table 3 below. Monkey 2B exhibited increased percentages of CD8 lymphocytes during and after treatment with mCRP as compared to the day 1 levels. Monkey 50B exhibited essentially unchanged percentages of CD8 lymphocytes during the treatment period and decreased percentages after treatment with mCRP was stopped.

TABLE 3

Determination Of CD8 Lymphocytes With Leu2a

| Monkey | Day | CD8 Lymphocytes | | % Change | |
|---|---|---|---|---|---|
| | | Absolute No. CD8 Cells Per µl* | % CD8 Cells | Absolute No. CD8 Cells Per µl | % CD8 Cells |
| 2B | 1 | 1926 | 59.1 | — | — |
| | 3 | 3586 | 71.0 | 86.2 | 20.1 |
| | 5 | 2551 | 65.1 | 32.5 | 10.2 |
| | 12 | 2708 | 63.3 | 40.6 | 7.1 |
| | 19 | 2446 | 68.7 | 27.0 | 16.2 |
| 50B | 1 | 2587 | 52.8 | — | — |
| | 3 | 2752 | 54.5 | 6.4 | 3.2 |
| | 5 | 2021 | 52.2 | −21.9 | −1.1 |
| | 12 | 2547 | 48.4 | −1.6 | −8.3 |
| | 19 | 1199 | 47.0 | −53.7 | −11.0 |

*Absolute numbers of CD8 lymphocytes determined by multiplying total number of lymphocytes and monocytes by percentage of CD8 cells.

Finally, the levels of 4B4 lymphocytes were measured. The results are presented in Table 4 below. The 4B4 marker is present on "memory" CD4 lymphocytes which respond to recall antigens. This population of cells is involved with the capacity of the immune system to mount a response to an antigen previously encountered by the immune system. "Naive" CD4 cells are those which are involved in "teaching" the immune system to mount a new response to an antigen.

In monkey 50B, the absolute number of 4B4 lymphocytes fluctuated above and below starting levels, but the percentages were constantly elevated during the nineteen-day test period (see Table 4). In monkey 2B, the absolute number of 4B4 lymphocytes was increased throughout the nineteen-day test period, while the percentages of 4B4 lymphocytes decreased and then increased to approximately the starting level (see Table 4).

TABLE 4

Determination Of 4B4 Lymphocytes

| Monkey | Day | 4B4 Lymphocytes | | % Change | |
|---|---|---|---|---|---|
| | | Absolute No. 4B4 Cells Per µl* | % 4B4 Cells | Absolute No. 4B4 Cells Per µl | % 4B4 Cells |
| 2B | 1 | 176 | 5.4 | — | — |
| | 3 | 202 | 4.0 | 14.8 | −25.9 |
| | 5 | 187 | 4.8 | 32.5 | −11.1 |
| | 12 | 195 | 4.6 | 40.6 | −15.6 |
| | 19 | 189 | 5.3 | 27.0 | −1.9 |
| 50B | 1 | 269 | 5.5 | — | — |
| | 3 | 310 | 6.1 | 6.4 | 12.0 |
| | 5 | 221 | 5.7 | −21.9 | 4.4 |
| | 12 | 358 | 6.8 | −1.6 | 24.1 |
| | 19 | 176 | 6.9 | −53.7 | 26.3 |

*Absolute numbers of 4B4 lymphocytes determined by multiplying total number of lymphocytes and monocytes by percentage of 4B4 cells.

As noted above, the blood samples drawn on days 1, 5 and 19 were subjected to routine hematological and blood chemistry tests. The results of the hematology and blood chemistries showed no significant changes and no adverse effects as a result of treatment with mCRP. All parameters remained within normal limits during the study.

Finally, no significant clinical abnormalities were observed as a result of treatment with mCRP. Indeed, both monkeys increased in body weight from day 1 to day 19 (the increases were 9% and 15%).

The amount of SIV p27 core protein in the plasma of the monkeys was determined using the COULTER™ SIV Core Ag Assay kit. The assay was performed according to the manufacturer's instructions. Briefly, the SIV Core Ag Assay is an enzyme immunoassay using a murine monoclonal antibody (anti-SIV core antigen p27) coated onto microwells. To perform the assay, 200 µl of each sample were added to an antibody-coated microwell, and the microwell strips were covered and incubated for 16–20 hours at room temperature. If present in the sample, the antigen will bind to the antibody-coated microwells. After the incubation period, the wells were washed six times with 300 µl Wash Buffer. Then, 200 µl of a biotinylated human antibody to SIV were added, and the strips were incubated for 1 hour at 37° C. The wells were again washed six times with 300 µl Wash Buffer. Next, 200 µl conjugated streptavidin horseradish peroxidase were added to each well, and the strips were incubated for 30 minutes at 37° C. The wells were again washed six times with 300 µl Wash Buffer. Next, 200 µl tetramethylbenzidine substrate were added to each well, and the strips were incubated for 30 minutes at room temperature. Color develops from the reaction of the peroxidase with hydrogen peroxide in the presence of the substrate, and the intensitiy of the color developed is directly proportional to the amount of SIV antigen present in the sample. The reaction was terminated by the addition of 50 µl of Coulter Stopping Reagent, and the strips were read on a microtiter plate reader at 450 nm. Values of p27 were obtained in ng/ml by comparison to a standard curve generated from samples supplied with the kit. Positive and negative controls were also run. A negative cutoff value was calculated. This negative cutoff value is the sum of the mean of the negative control wells (diluent only) and a predetermined factor of 0.03. Samples with absorbance values greater than or equal to the cutoff value are considered positive for SIV antigen.

The results are presented in Table 5 below. Plasma antigen levels were below detectable limits in both monkeys at all time points of the study. The mean negative control absorbance was 0.038, and the Coulter negative cutoff was calculated to be 0.068. No absorbance values were greater than the cutoff value.

TABLE 5

Plasma Antigen Levels

| Monkey | Plasma p27 Antigen (ng/ml) | | | | |
|---|---|---|---|---|---|
| | Day 1 | Day 3 | Day 5 | Day 12 | Day 19 |
| 2B | 0.043 | 0.047 | 0.037 | 0.019 | 0.016 |
| 50B | 0.032 | 0.037 | 0.002 | 0.009 | 0.008 |

Figure 2A:
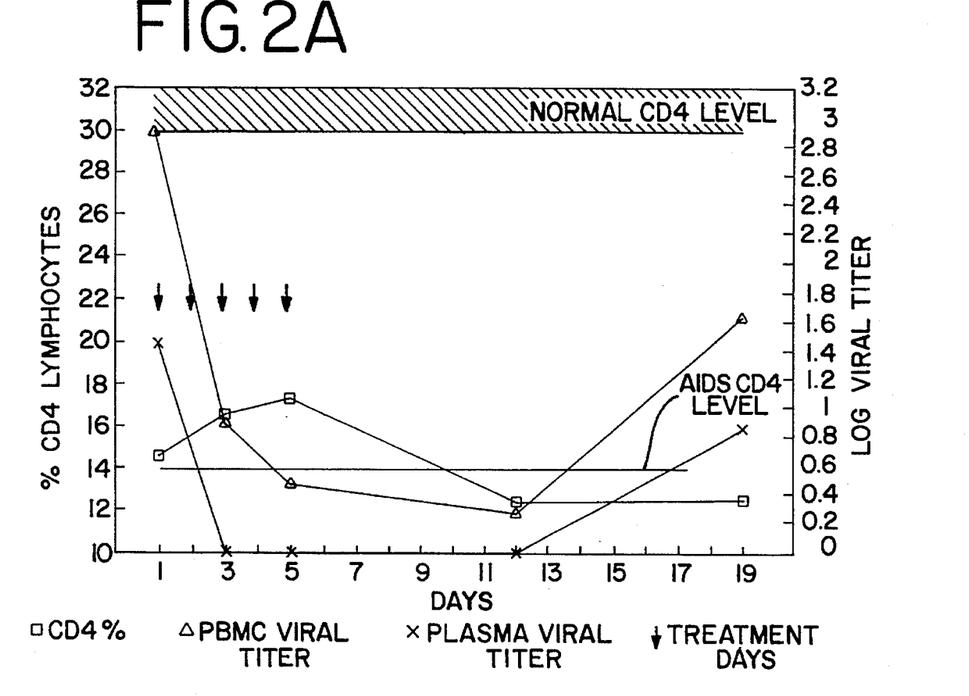
FIGS. 2A and 2B: Graphical representations of percent CD4 lymphocytes and $\log_{10}$ of SIV titer in peripheral blood mononuclear cells (PBMC) and plasma for monkey 2B (FIG. 2A) and monkey 50B (FIG. 2B) versus time. The arrows indicate the days on which mCRP was administered to the monkeys.
Figure 2B:
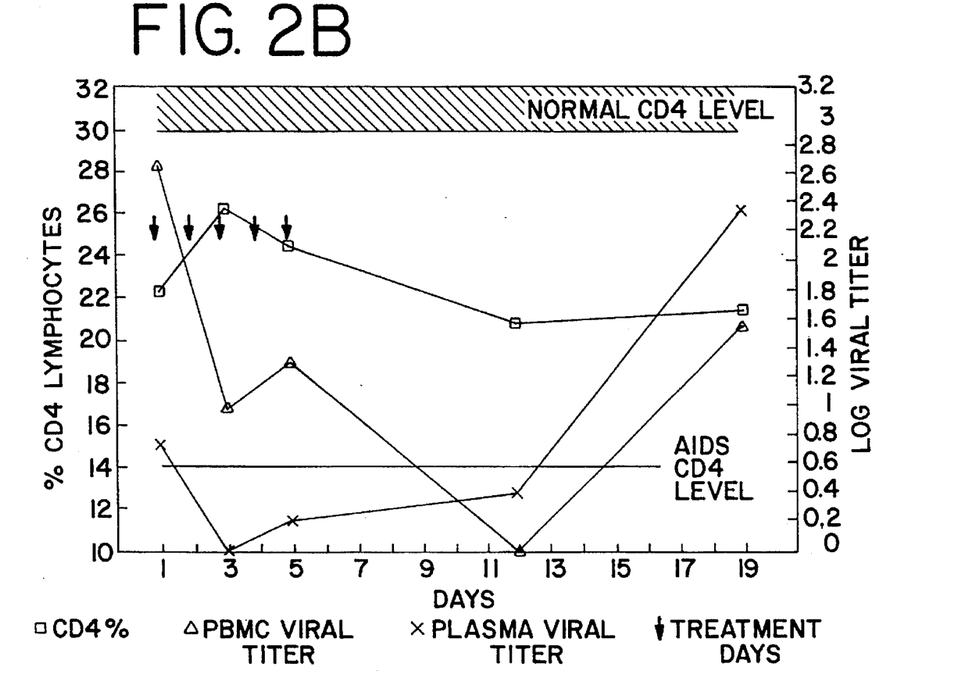

Virus titrations were performed on blood samples drawn sterilely in preservative-free heparin as follows. Peripheral blood mononuclear cells (PBMC) were separated from the blood using Ficoll-Paque. Six four-fold dilutions of PBMC beginning with $3.14 \times 10^4$ cells and six four-fold dilutions of plasma beginning with 50 µl were co-cultured with CEMX174 cells in 96-well microtiter plates (total volume 250 µl and total number of CEMX174 cells $2.5 \times 10^4$). Cultures supernatant samples were collected on day 14. Cultures were tested for p27 antigen as described above. All cultures were run in 6 replicates. A negative cutoff point was calculated as described above for each assay plate using uninfected cell culture supernatants as the negative control. Each well was assigned as positive or negative by comparison to the cutoff. Individual virus titers were calculated by the method of Reed and Muench, *Amer. J. Hygiene*, 27, 493 (1938) by summing the replicate values. The negative of the log titer that was thus calculated is plotted versus time in FIGS. 2A and 2B. FIGS. 2A and 2B also show the CD4 lymphocyte levels (using OKT4a).

As can be seen from FIGS. 2A and 2B, there was a dramatic drop in virus titer measured in both PBMC and plasma in each monkey upon treatment with mCRP. The change was greatest for the PBMC titers which decreased approximately 2.0 logs for monkey 50B and 1.5 logs for monkey 2B. The viral titer remained low for about one week after the last dose of mCRP, but then began to climb again. The level of p27 antigen in plasma showed a similar pattern.

From the above, it can be concluded that injection of mCRP into SIV-infected monkeys dramatically decreased cell-associated and plasma SIV virus titers. mCRP also increased the percent CD4 lymphocytes in SIV-infected monkeys during treatment with mCRP. The mCRP treatment did not cause any side effects.

I claim:

1. A method of treating an HIV-1 viral infection in a mammal comprising administering an effective amount of modified-C-reactive protein (modified-CRP) to the mammal.

* * * * *